(12) United States Patent
Tanabe (10) Patent No.: US 7,846,696 B2
(45) Date of Patent: Dec. 7, 2010

(54) METHOD FOR ESTIMATING TARGET NUCLEIC ACID RATIO

(75) Inventor: Tetsuya Tanabe, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/498,771

(22) Filed: Jul. 7, 2009

(65) Prior Publication Data

US 2010/0009372 A1 Jan. 14, 2010

(30) Foreign Application Priority Data

Jul. 10, 2008 (JP) .............................. 2008-180412

(51) Int. Cl.
*C12P 19/34* (2006.01)

(52) U.S. Cl. .................................... 435/91.2

(58) Field of Classification Search ................. 435/91.2
See application file for complete search history.

(56) References Cited

U.S. PATENT DOCUMENTS 5,595,890 A 1/1997 Newton et al.

2008/0064028 A1 3/2008 Hirao et al.

FOREIGN PATENT DOCUMENTS

| JP | 2853864 B2 | 2/1999 |
| JP | 3950546 B2 | 8/2007 |
| WO | 2004/101794 A1 | 11/2004 |

OTHER PUBLICATIONS

Cottrez et al. Nucleic Acids Research, vol. 22, No. 13, pp. 2712-2713, 1994.*
J. K. Kulski, "End-Point Titration-PCR for Quantitation of Cytomegalovirus DNA," Methods of Molecular Medicine, vol. 26, pp. 119-130, Apr. 28, 1999.

* cited by examiner

*Primary Examiner*—Samuel Woolwine
*Assistant Examiner*—Cynthia B Wilder
(74) *Attorney, Agent, or Firm*—Westerman, Hattori, Daniels & Adrian, LLP (57) ABSTRACT

A method is disclosed for estimating a ratio between the amount of target nucleic acid and the amount of the reference nucleic acid in the examined nucleic acid samples from the PCR reaction solutions at the endpoint.

18 Claims, 4 Drawing Sheets

| | | | |
|---|---|---|---|
| gcatctttat | tatggcagag | agaattttct | gaactattta |
| tggacaacag | tcaaacaaca | attctttgta | cttttttttt |
| tccttagtct | ttctttgaag | cagcaagtat | gatgagcaag |
| ctttctcaca | agcatttggt | tttaaattat | ggagtatgt[g/t] |
| tctgtggaga | cgagagtaag | taaaactaca | ggctttctaa |
| tgcctttctc | agagcatctg | tttttgttta | tatagaaaat |
| tcagtttcag | gatcacagct | aggtgtcagt | gtaaactata |
| atttaacagg | agttaagtat | ttttgaaact | gaaaacactg |
| taggactatt | cagttatatc | ttgtgaaaaa | ggaaagcaat |
| gaagtt | | | |

METHOD FOR ESTIMATING TARGET NUCLEIC ACID RATIO

BACKGROUND OF THE INVENTION

1. Field of the Invention

The present invention is directed to a method for estimating the ratio of a target nucleic acid to the total amount of target nucleic acid and reference nucleic acid in the examined nucleic acid samples based on the amounts of amplification products in the reaction solutions at the endpoint of PCR reaction.

2. Description of the Related Art

Genetic examinations by analysis of nucleic acids are widely employed for medical, research, and industrial applications with recent progress in technologies of genetic manipulation, genetic recombination, and the like. These examinations are examinations that involve the detection and quantification of the presence of a target nucleic acid having a target nucleotide sequence in samples, and are applied in various fields, not only in the diagnoses and treatment of diseases, but also in examination of food. For example, genetic examinations for detecting congenital or acquired mutant genes, virus-related genes, and others are carried out for diagnosis of diseases, such as genetic diseases, tumors, and infections. Analysis of genetic polymorphisms, including single nucleotide polymorphism (SNP), is also applied not only to clinical examinations and academic research, but also to quality checks and traceability of foods and others.

Samples which are subjected to gene analysis are often of trace amounts, like specimens in clinical examinations. For this reason, genome fragments containing a target nucleic acid which is an objective of analyzation are usually amplified in advance by, for example, PCR (Polymerase Chain Reaction), and the amplified genome fragments are employed to detect and quantify the target nucleic acid. Methods for measuring the amount of a target nucleic acid in examined samples which is an objective to be analyzed, in general, involve preparing a series of samples containing the target nucleic acid at known concentrations, making a calibration curve by measuring the amounts of amplified products in the reaction solutions after the PCR reaction performed on this series, and determining, on the basis of this calibration curve, the amount of the target nucleic acid in the examined samples.

On the other hand, samples which are subjected to gene analysis are mostly living-body samples and thus are prone to being influenced by, for example, individual differences due to subjects from which the samples were taken, where and when the samples were taken, and methods for preparing and storing the samples. As a result, there are great variations among the samples and it is also difficult in many cases to compare the results of examinations. However, analysis can be made with high accuracy by using, as a reference nucleic acid, a nucleic acid which is relatively abundant in samples or a nucleic acid having a known content which can be expected beforehand, and determining the ratio between the amount of target nucleic acid and the amount of reference nucleic acid. For example, when the amount of target nucleic acid in two samples are compared, it is possible to ascribe the difference in the amounts of target nucleic acid in the two samples to significant difference between the sample, rather than sample variations between the samples, by comparing the ratio between the amount of target nucleic acid and the amount of reference nucleic acid in each of the samples, rather than comparing directly the amounts of target nucleic acid.

Methods for determining the ratio between the amount of target nucleic acid and the amount of reference nucleic acid in samples include, for example, competitive PCR processes in which at the endpoint of PCR, the amounts of amplification of target nucleic acid and of reference nucleic acid are compared and quantified to determine the ratio between the target nucleic acid and the reference nucleic acid. As a method for determining the ratio between the amount of target nucleic acid and the amount of reference nucleic acid in samples is disclosed, for example, (1) a method for determining the ratio between the types of nucleic acids in a group of nucleic acid samples, the method including the steps of amplifying in a gene amplification process mixtures of the respective nucleic acids in the group of nucleic acid samples; digesting the amplified products with a restriction enzyme; subjecting the digested products to electrophoresis; measuring the density of migrated bands; and determining the ratio between the types of nucleic acids in the group of nucleic acid samples based on the densities of the respective bands measured (see, for example, Japanese Patent No. 3,950,546). Also disclosed is (2) a method for quantifying a particular plant genus in foods or others, the method including preparing a correcting sample, in which a sample derived from the particular plant genus which is an objective to be detected and a sample of a standard plant are mixed at a predetermined ratio, followed by extracting genome DNAs from the correcting sample; preparing a sample to be examined, in which a known amount of the standard plant sample is added to a food or raw material of food which is an objective to be examined, followed by extracting genome DNAs from the sample to be examined; performing a real time PCR process with the genome DNAs and primers; and making a correction with a correcting reference value which is detected in the correcting sample, thereby determining by calculation the amount of raw material from the particular plant contained in the examined sample (see, for example, PCT International Publication No. WO 04/101794).

Competitive PCR processes are based on the assumption that the ratios between a reference nucleic acid and a target nucleic acid in the reaction solutions before the PCR reaction (initial template amount ratio) and after the PCR reaction (post-amplification template amount ratio) are almost equal, that is, that the reference nucleic acid and the target nucleic acid are amplified with the same efficiency. Thus, competitive PCR processes have a problem resulting in unreliable measured results when a reference nucleic acid and a target nucleic acid are amplified with different efficiencies.

PCR reactions, in principle, amplify a particular target nucleotide sequence by repeating 25 to 30 cycles, each cycle consisting of three steps: denaturation, annealing, and extension. At early reaction cycles, the target nucleic acid will be amplified $2^n$ times after the cycle has been repeated n times and increased exponentially, whereas at the end of the reaction (endpoint), the PCR reaction will have become saturated. That is to say, the amounts of amplified product in the reaction solutions at the endpoint are not correlated with the amount of target nucleic acid at the beginning of the PCR reaction, and it is difficult to make a quantitative measurement. Therefore, the above-described method (1) in which the amplification product is detected and quantified in the reaction solutions at the endpoint has a problem of being incapable of making a measurement in the case where the PCR reaction is in saturation. On the other hand, the above-described method (2) employs real time PCR and thus does not pose a problem resulting from the saturation of the PCR reaction, but unlike common PCR, real time PCR has problems of requiring a more expensive apparatus and intricate considerations of reaction conditions.

SUMMARY OF THE INVENTION

An object of the present invention is to provide a method by which the ratio between the amount of target nucleic acid and the amount of reference nucleic acid in the reaction solutions at the beginning of the PCR reaction can be determined with high accuracy and simply from the reaction solutions at the endpoint of the PCR reaction.

The present inventors have conducted extensive research in order to solve the above-described problems, with the result that the present inventors have found that a continuously differentiable function of the primer consumption rate in the reaction solutions at the endpoint (ratio of the primer consumed in the PCR amplification to the amount of primer added to the reaction solution) is defined as a function of a mixing ratio of a target nucleic acid and a reference nucleic acid, independently for each of the target nucleic acid and the reference nucleic acid, and then, by employing these functions, the ratio of the target nucleic acid to the total amount of target nucleic acid and reference nucleic acid in examined samples can be determined from the primer consumption rate in the reaction solutions at the endpoint when a PCR reaction is carried out under the same conditions on samples to be examined, and have arrived at the completion of the present invention. Here, since the amount of primer consumed in the PCR amplification corresponds to the amount of amplified product, the primer consumption rate can be determined as the proportion of the amount of amplified product to the amount of primer added to the reaction solution.

Therefore, the present invention provides:

(1) a method for estimating a molar ratio of a target nucleic acid to the total amount of the target nucleic acid and a reference nucleic acid in an examined sample, the method comprising the steps of:

(a) preparing a standard nucleic acid sample series having different mixing ratios (molar ratios) of the target nucleic acid to the total amount of the target nucleic acid and the reference nucleic acid;

(b) carrying out steps (i) and (ii) described below, on each standard nucleic acid sample of the standard nucleic acid sample series prepared in the step (a);

(c) calculating a first continuously differentiable function and a second continuously differentiable function, wherein the first continuously differentiable function approximates the relationship between the mixing ratios and the amount of amplified product derived from the target nucleic acid which are obtained in the step (b), and wherein the second continuously differentiable function approximates the relationship between the mixing ratios and the amount of amplified product derived from the reference nucleic acid which are obtained in the step (b);

(d) carrying out steps (i) and (ii) described below, on a sample to be examined; and (e) estimating the ratio of the target nucleic acid to the total amount of the target nucleic acid and the reference nucleic acid in the examined sample, from the amount of amplified product derived from the target nucleic acid and the amount of amplified product derived from the reference nucleic acid which are obtained in the step (d), and the first continuously differentiable function and the second continuously differentiable function which are obtained in the step (c);

wherein the step (i) comprises performing PCR (Polymerase Chain Reaction) reaction in reaction solutions containing the nucleic acid sample, a detecting primer for target nucleic acid, and a detecting primer for reference nucleic acid, and wherein the step (ii) comprises measuring, after the step (i), the amount of amplified product derived from the target nucleic acid and the amount of amplified product derived from the reference nucleic acid;

(2) the method for estimating a target nucleic acid ratio according to (1), wherein the step (i) is a step (i') in which the PCR reaction is performed separately in a reaction solution containing the nucleic acid sample and the detecting primer for target nucleic acid and in a reaction solution containing the nucleic acid sample and the detecting primer for reference nucleic acid;

(3) the method for estimating a target nucleic acid ratio according to (1) or (2), wherein the detecting primer for target nucleic acid and the detecting primer for reference nucleic acid are primers labeled with fluorescent substances;

(4) the method for estimating a target nucleic acid ratio according to (3), wherein measuring the molar ratio of the amount of the amplified product in the reaction solutions after the PCR reaction to the amount of the primer in the reaction solutions before starting the PCR reaction in the reaction solution is carried out employing one or more analyses selected from the group consisting of fluorescence correlation spectroscopy, fluorescence intensity distribution analysis, and fluorescence intensity distribution analysis-polarization;

(5) the method for estimating a target nucleic acid ratio according to any one of (1) to (3), wherein measuring the amount of the amplified product is carried out by employing a DNA binding dye;

(6) the method for estimating a target nucleic acid ratio according to any one of (1) to (3), wherein measuring the amount of the amplified product is carried out by employing a hybridization probe labeled with a fluorescent substance;

(7) the method for estimating a target nucleic acid ratio according to any one of (1) to (3), wherein measuring the amount of the amplified product is carried out by employing a FRET hybridization probe, a molecular beacon, or a TaqMan probe;

(8) the method for estimating a target nucleic acid ratio according to any one of (1) to (7), wherein the target nucleic acid is a nucleic acid derived from a mutated cell and the reference nucleic acid is a nucleic acid derived from a normal cell;

(9) the method for estimating a target nucleic acid ratio according to any one of (1) to (7), wherein the target nucleic acid is a nucleic acid derived from a gene to be examined which a mutated cell possesses and the reference nucleic acid is a nucleic acid derived from the same gene to be examined which a normal cell possesses;

(10) the method for estimating a target nucleic acid ratio according to (9), wherein the gene to be examined is a gene selected from the group consisting of the EGFR (Epidermal Growth Factor Receptor) gene, the JAK2 gene, and the Bcr-Ab1 gene;

(11) the method for estimating a target nucleic acid ratio according to any one of (1) to (7), wherein the target nucleic acid is a nucleic acid having a sequence comprising one type of genetic polymorphisms and the reference nucleic acid is a nucleic acid having a sequence comprising a polymorphic site of a type different from the type of the genetic polymorphisms;

(12) the method for estimating a target nucleic acid ratio according to (11), wherein the genetic polymorphisms are single nucleotide polymorphisms;

(13) the method for estimating a target nucleic acid ratio according to (11) or (12), wherein the gene polymorphisms are mitochondrial DNA polymorphisms;

(14) the method for estimating a target nucleic acid ratio according to any one of (1) to (7), wherein the target nucleic acid is a nucleic acid derived from a parasitic organism and the reference nucleic acid is a nucleic acid derived from a host organism;

(15) the method for estimating a target nucleic acid ratio according to (14), wherein the parasitic organism is a bacterium or a virus;

(16) the method for estimating a target nucleic acid ratio according to any one of (1) to (7), wherein the target nucleic acid is a nucleic acid derived from a genetically modified plant and the reference nucleic acid is a nucleic acid derived from a genetically non-modified plant.

By employing the inventive methods for estimating the target nucleic acid ratio, the ratio of a target nucleic acid to the total amount of target nucleic acid and reference nucleic acid in the reaction solutions before starting the PCR reaction can be determined very simply, using the reaction solutions at the endpoint of the PCR reaction. Because amplification curves of a target nucleic acid and of a reference nucleic acid are independently handled, the ratio of the target nucleic acid can be determined with high accuracy, even if the target nucleic acid and the reference nucleic acid are amplified with significantly different efficiencies.

DETAILED DESCRIPTION OF THE INVENTION

The inventive methods for estimating the target nucleic acid ratio are methods by which a PCR reaction is performed using, as a template, a nucleic acid in a nucleic acid sample to be examined and the reaction solutions are analyzed at the endpoint, thereby estimating the ratio of the target nucleic acid to the total amount of target nucleic acid and reference nucleic acid (hereinafter sometimes referred to simply as "target nucleic acid ratio") in the reaction solutions before the PCR reaction, that is, the nucleic acid samples to be examined. In the present invention and in the specification, unless described specifically, "amount," "amount ratio" and "proportion", and "ratio" mean "molar amount," "molar proportion," and "molar ratio," respectively The amplification of PCR reactions progresses exponentially at early amplification stages, but at later amplification stages, will be decreased due to various causes, such as decreased primer concentration, template reassociation, and reduced enzyme activity, and the reaction will become saturated. As a result, the amount ratios between reference nucleic acid and target nucleic acid in the reaction solutions at the endpoint of the PCR reaction often do not reflect the ratio before the PCR reaction. However, employing the inventive methods for estimating the target nucleic acid ratio allows one to estimate with accuracy the ratio of the reference nucleic acid and the target nucleic acid in the reaction solutions before the PCR reaction by analyzing the reaction solutions at the endpoint, when a detecting primer for target nucleic acid and a detecting primer for reference nucleic acid are primers that have complimentary reactivity to each other.

Here, "a detecting primer for target nucleic acid and a detecting primer for reference nucleic acid are primers that have complimentary reactivity to each other" means primers having a relation in which when reactions with one primer approach the saturation, the other has not reacted, and that the amount of target nucleic acid and the amount of reference nucleic acid in the examined nucleic acid samples have a negative correlation. Since a detecting primer for target nucleic acid and a detecting primer for reference nucleic acid have complimentary reactivity to each other, when one of the PCR reaction of target nucleic acid and the PCR reaction of reference nucleic acid has become saturated, the other has not reached saturation at the endpoint of the PCR reactions. Therefore, it is possible, for example, in cases where the PCR reaction of reference nucleic acid is in saturation and the PCR reaction of target nucleic acid has not reached the saturation, to determine the ratio of the target nucleic acid to the total amount of target nucleic acid and reference nucleic acid in the reaction solutions before the PCR reaction from the amount of amplified product of the target nucleic acid (the reaction amount of the detecting primer for target nucleic acid).

In general, there are small differences in gene sequences between mutated cells and normal cells and in many cases, only a small number of bases are different. It is possible, by designing primers from a common sequence around a mutated site of interest and performing amplification, to prepare samples having particular concentrations which retain the ratio between nucleic acids derived from mutated cells and from normal cells. In this case, because the amplification reactions of a nucleic acid derived from mutated cells and of a nucleic acid derived from normal cells employ the same primer, and thus their efficiencies of amplification are likely to be equal, and because the amounts of nucleic acids in the samples are constant at the end of the amplification reaction, regardless of their mixing ratios, the amount of nucleic acid derived from mutated cells and the amount of nucleic acid derived from normal cells have a negative correlation. In the inventive methods for estimating the target nucleic acid ratio, therefore, it is possible, by using a nucleic acid derived from mutated cells as a target nucleic acid and a nucleic acid derived from normal cells as a reference nucleic acid, to determine the ratio of the amount of nucleic acid derived from mutated cells to the total amount of nucleic acid derived from mutated cells and nucleic acid derived from normal cells in the examined nucleic acid sample, that is, the mutation ratio. Therefore, the inventive method for estimating a target nucleic acid ratio is suitable for testing the mutation ratio in a gene of an individual from which a nucleic acid sample to be examined was taken.

In the present invention, mutated cells are not limited specifically, if they are cells in which a mutation or mutations have been caused in a gene, and may be cells in which an acquired mutation or mutations have been caused, such as tumor cells, or cells in which a congenital mutation or mutations have resulted. For example, when a tumor cell is used as a mutated cell, the mutation ratio determined by the inventive method for estimating a target nucleic acid ratio is highly reliable and thus can be expected to be capable of being used as an indicator for the diagnosis of the degree of progression of the tumor.

In the present invention, it is preferable that the target nucleic acid is a nucleic acid derived from a gene to be examined which a mutated cell possesses and the reference nucleic acid is a nucleic acid derived from the same gene to be examined which a normal cell possesses. In cases where the target nucleic acid and the reference nucleic acid are derived from the same gene to be examined, target nucleic acid ratios having higher reliability can be obtained, because there is a strong correlation between the amount of target nucleic acid and the amount of reference nucleic acid. For example, when the mutated cells are tumor cells, it is possible to use, as a gene to be examined, genes in which a mutation or mutations are detected at high frequencies in tumor cells, such as the EGFR (Epidermal Growth Factor Receptor) gene, the JAK2 gene, and the Bcr-Ab1 gene.

In genetic polymorphisms, if a gene of an individual is a homoallele containing one type of genetic polymorphisms, the individual will not have an allele containing another type of the genetic polymorphisms. That is, the amounts of a nucleic acid containing one particular type and a nucleic acid containing another type of the genetic polymorphisms have a negative correlation. Therefore, in the inventive methods for estimating the target nucleic acid ratio, it is possible, by using, as a target nucleic acid, a nucleic acids having a sequence containing one type of genetic polymorphisms, and as a reference nucleic acid, a nucleic acids having a sequence containing a polymorphic site which is of a different type of the genetic polymorphisms from that of the target nucleic acid, to determine the ratio of the respective types in nucleic acids derived from the genetic polymorphisms in the examined nucleic acid samples. Therefore, the inventive methods for estimating the target nucleic acid ratio are also suitable for typing genetic polymorphisms in an individual from whom a nucleic acid sample to be examined was taken. Especially for genetic polymorphisms in mitochondria, it is known that mitochondria are present in tens to thousands of copies within a cell and the mixing ratio between normal and mutated types is varied, and thus the quantitative method of the present invention is suitable.

In the present invention, the genetic polymorphisms are not limited specifically, if the nucleotide sequence of a gene is different from individual to individual within a group of a particular species of organisms. The genetic polymorphisms include, for example, single nucleotide polymorphisms (SNPs) and microsatellites. Also included can be genetic polymorphisms of genome DNA and mitochondrial DNA polymorphisms.

In addition, in the present invention, it is possible, by using a nucleic acid derived from a parasitic organism as a target nucleic acid and a nucleic acid derived from a host organism as a reference nucleic acid, to determine the ratio of the amount of nucleic acid derived from the parasitic organism to the total amount of nucleic acid derived from the host organism and nucleic acid derived from the parasitic organism in the examined nucleic acid sample, that is, the parasitic ratio. The parasitic organisms are not limited specifically, and preferably are bacteria and viruses. When parasitic organisms are infection causing organisms, the inventive methods for estimating the target nucleic acid ratio are also suitable for testing infection ratios of infections.

Also, in the present invention, it is possible, by using a nucleic acid derived from a genetically modified plant as a target nucleic acid and a nucleic acid derived from a genetically non-modified plant as a reference nucleic acid, to determine the ratio of the amount of nucleic acid derived from the genetically modified plant to the total amount of nucleic acid derived from the genetically modified plant and nucleic acid derived from the genetically non-modified plant in the examined nucleic acid sample, that is, the content of the nucleic acid derived from the genetically modified plant. It is preferable that a genetically non-modified plant from which a nucleic acid is used as a reference nucleic acid is a plant of the same variety as the genetically modified plant. For example, it is possible, by using a nucleic acid derived from native maize as a reference nucleic acid and a nucleic acid derived from genetically modified maize as a target nucleic acid, to determine the content ratio of the genetically modified maize in a given amount of corn.

Furthermore, it is possible, by amplifying in advance a target nucleic acid and a reference nucleic acid in nucleic acid samples to be examined using a common primer, to prepare samples having a negative correlation between the amount of target nucleic acid and the amount of reference nucleic acid. Because employing a common primer results in amplifying of the target nucleic acid and the reference nucleic acid with the same efficiency of amplification, the ratio between the amount of target nucleic acid and the amount of reference nucleic acid in the examined nucleic acid samples (target nucleic acid ratio), in theory, will not be affected by amplification. Thus, it is possible, by employing samples having a negative correlation between the amount of target nucleic acid and the amount of reference nucleic acid by amplifying in advance nucleic acid samples to be examined, to estimate the ratio between the target nucleic acid and the reference nucleic acid by employing the inventive method for estimating a target nucleic acid ratio. For example, in cases where a nucleic acid derived from a parasitic organism is used as a target nucleic acid, it is possible that the reference nucleic acid is a nucleic acid derived from a host organism which has a sequence analogous to the target nucleotide sequence, and the nucleic acid derived from the parasitic organism and the nucleic acid derived from the host organism are amplified at the same time with the identical primer, thereby preparing samples which have a negative correlation between the nucleic acid derived from the parasitic organism and the nucleic acid derived from the host organism. Also, in cases where a nucleic acid derived from a genetically modified plant is used as a target nucleic acid, it is possible that a primer is designed from a common sequence around the genetic recombination site and amplification is performed with this primer, thereby preparing samples which have a negative correlation between the nucleic acid derived from the genetically modified plant and the nucleic acid derived from the genetically non-modified plant, while retaining their ratio.

In the present invention, a detecting primer for target nucleic acid means a primer which is employed to PCR amplify a target nucleic acid having a target nucleotide sequence and which does not recognize a reference nucleic acid having a reference sequence and recognizes specifically the target nucleic acid. Similarly, in the present invention, a detecting primer for reference nucleic acid means a primer which is employed to PCR amplify a reference nucleic acid and which does not recognize a target nucleic acid and recognizes specifically the reference nucleic acid.

For example, in cases where a nucleic acid derived from a mutated cell is used as a target nucleic acid and a nucleic acid derived from a normal cell is used as a reference nucleic acid, it is possible that primers which can specifically recognize a nucleic acid having a partial sequence of a gene that contains a mutated site (site at which a mutation has been caused) are used as a detecting primer for target nucleic acid, and primers which can specifically recognize a partial sequence of a normal gene that contains a site corresponding to the mutated site are used as a detecting primer for a reference nucleic acid. In cases where a nucleic acid which has a sequence containing one type of genetic polymorphisms is used as a target nucleic acid and a nucleic acid which has a sequence containing a polymorphic site of a different type of the genetic polymorphisms from that of the target nucleic acid is used as a reference nucleic acid, it is possible that primers which can specifically recognize a nucleic acid having a partial sequence of a gene that contains a genetic polymorphism site of each type are used as a detecting primer for a target nucleic acid or for a reference nucleic acid.

PCR reactions employ two types of primers which hybridize at both ends of a region of nucleic acid to be amplified (a forward primer and a reverse primer corresponding thereto), and both of a detecting primer for a target nucleic acid and a detecting primer for a reference nucleic acid may be either forward primers or reverse primers. In cases where a detecting primer and a corresponding reverse primer for a target nucleic acid are employed in order to PCR amplify the target nucleic acid, and a detecting primer and a corresponding reverse primer for a reference nucleic acid are employed in order to PCR amplify the reference nucleic acid, the same primer may be employed in common as a reverse primer for the target nucleic acid or as a reverse primer for the reference nucleic acid.

These primers can be designed employing any methods well-known in the art. For example, known genome sequence data and generally used primer-designing tools can be employed to easily design primers. Such primer-designing tools include, for example, Primer 3 available at a web (Rozen, S., H. J. Skaletsky, 1996, www-genome.wi.mit.edu/genome_software/other/primer3.html), Visual OMP (DNA Software, Inc.), and others. Known genome sequence data are usually available from international databases of nucleotide sequences, such as NCBI (National Center for Biotechnology Information), CCBJ (DNA Data Bank of Japan), and the like.

Primers thus designed can be synthesized employing any methods well-known in the art. For example, one may request oligo synthesis suppliers to synthesize primers, or synthesize primers by oneself employing a commercially available synthesizer. The primers can possess, in addition to the region hybridizing to the target nucleic acid or the like, additional sequences to such a degree that they do not inhibit the PCR amplification of the target nucleic acid and others. Such additional sequences include, for example, recognition sequences of restriction enzymes, sequences subjected to labeling of nucleic acids, and others.

Furthermore, the detecting primer for target nucleic acid and the detecting primer for reference nucleic acid which are employed in the present invention may be labeled primers in order to make it easy to detect and analyze amplified products and unreacted primers. Substances for such labeling are not limited specifically, if they can be employed to label nucleic acids, and include radioactive isotopes, fluorescent substances, chemiluminescent substances, biotin, and the like. It is preferable that the detecting primer for target nucleic acid and the detecting primer for reference nucleic acid which are employed in the present invention are primers labeled with fluorescent substances, because such primers have high sensitivity and allow easy detection. As the fluorescent substance, for example, substances generally used for labeling nucleic acids, such as FITC, fluorescein, rhodamine, and the like can be selected and employed as appropriate.

In particular, the inventive methods for estimating the target nucleic acid ratio are methods for estimating the ratio of the target nucleic acid to the total amount of target nucleic acid and reference nucleic acid in the examined nucleic acid samples, wherein the methods are characterized by carrying out the following steps (a) to (e). The following describes the inventive method for each of these steps.

First, in step (a), a standard nucleic acid sample series is prepared which has different mixing ratios of a target nucleic acid to the total amount of target nucleic acid and reference nucleic acid (hereinafter sometimes abbreviated to "mixing ratios"). The number of standard nucleic acid samples constituting a standard nucleic acid sample series is not limited specifically, and preferably is on the order of three to twenty. The mixing ratio of each of the standard nucleic acid samples is not limited specifically, and can be selected as appropriate with consideration given to the type of detecting primer for target nucleic acid and detecting primer for reference nucleic acid which are employed, and others. For example, the mixing ratio of each of the standard nucleic acid samples may be set at equal intervals, as in a standard nucleic acid sample series which consists of five standard nucleic acid samples having mixing ratios of 0, 0.25, 0.5, 0.75, and 1.0. Alternatively, the mixing ratio of each of the standard nucleic acid samples may be set at unequal intervals as in a standard nucleic acid sample series which consists of nine standard nucleic acid samples having mixing ratios of 0, 0.05, 0.1, 0.2, 0.5, 0.8, 0.9, 0.95, and 1.0. Because the present invention is for determining the target nucleic acid ratio at the endpoint where there is an increased possibility that the PCR reaction has become saturated, it is preferable that standard nucleic acid sample series which are employed are those in which mixing ratios, at which any one of the target nucleic acid and the reference nucleic acid will approach saturation, are set at smaller intervals in the ranges of 0 to 0.2 and 0.8 to 1.0.

Each of the standard nucleic acid samples constituting the standard nucleic acid sample series is employed as the template in the PCR reaction, and it is necessary that when a standard nucleic acid sample having a mixing ratio of zero or near zero is used as the template, the PCR reaction of the reference nucleic acid will approaches the saturation, and on the contrary, when a standard nucleic acid sample having a mixing ratio of one or near one is used as the template, the PCR reaction of the target nucleic acid approaches the saturation. Therefore, it is preferable that the sum of the amount of target nucleic acid and the amount of reference nucleic acid in each of the standard nucleic acid samples is adjusted as appropriate, with consideration given to their amounts added to the reaction solutions, and others, so that the amount of template is sufficient when they are added to reaction solutions for the PCR reaction.

Next, in step (b) are carried out the following steps: (i) performing PCR reaction on each standard nucleic acid sample of the standard nucleic acids sample series prepared in step (a), in reaction solutions containing a nucleic acid sample, a detecting primer for target nucleic acid, and a detecting primer for reference nucleic acid; and subsequently (ii) measuring, after the step (i), the amount of amplified product derived from the target nucleic acid and the amount of amplified product derived from the reference nucleic acid.

In step (i), reaction conditions in each PCR reaction, such as the composition of reaction solutions and the thermal cycle, are not limited specifically and can be determined as appropriate, with consideration given to the Tm values of primers used, such as the detecting primer for target nucleic acid, and the type of DNA polymerases etc. Each PCR reaction, however, must be under the same reaction conditions in all respects, except that the type of the standard nucleic acid samples which are added to the reaction solutions is different.

In theory, since the amount of amplified product is equal to the amount of primer consumed in the reaction, it is possible that by determining the amount of each amplified product, the primer consumption rate, which is a molar ratio of the amount of amplified product in the reaction solution after the PCR reaction to the amount of primer in the reaction solution before starting the PCR reaction, is calculated for each of the detecting primer for target nucleic acid and the detecting primer for reference nucleic acid. Specifically, the primer consumption rate is expressed by the following equation:

Primer consumption rate =[amount of amplified product]/[initial primer amount]=[amount of amplified product]/([amount of amplified product]+[amount of unreacted primer])

where "initial primer amount" means the amount of primer in the reaction solution before starting the PCR reaction (amount of primer added to the reaction solution).

Thus, in order to determine the primer consumption rate, one may measure the amount (moles) in itself of an amplified product in the reaction solution after the PCR reaction, followed by dividing the amount of the amplified product by the initial primer amount (moles). Alternatively, the ratio between the amounts of the amplified product and the unreacted primer after the PCR reaction may be measured and then the primer consumption rate can be also determined by calculation from this ratio, based on the above-described equation.

Methods for measuring the amount (moles) of an amplified product in a reaction solution are not limited specifically, and can be selected and carried out as appropriate, from known methods employed for quantitatively measuring the amount of an amplified product. For example, amplified products may be detected with hybridization probes which are labeled with DNA binding dyes, such as SYBER GREEN, or fluorescent substances. It is also possible to employ probes for detection, such as FRET hybridization probes, molecular beacons, and TaqMan probes, which carry both of a fluorescent chromogenic substance and a quencher bound thereto, result in a sufficiently increased distance between the fluorescent chromogenic substance and the quencher by binding specifically to an amplified product, thereby emitting fluorescence, and allow one to quantitatively detect the amplified product by measuring the amount of emitted fluorescence. Design and synthesis of these primers can be carried out routinely. From measurements obtained by these procedures, the amount (moles) of amplified product can be determined by employing a calibration curve which is made routinely with amplified products having concentrations known in advance.

In addition, in cases where the detecting primer for target nucleic acid and the detecting primer for reference nucleic acid are primers labeled with fluorescent substances, it is preferable that the ratio between the amounts of the amplified product and the unreacted primer in the reaction solution after the PCR reaction is measured by employing one or more analyses selected from the group consisting of Fluorescence Correlation Spectroscopy (hereinafter referred to as FCS), Fluorescence Intensity Distribution Analysis (hereinafter referred to as FIDA), and FIDA-polarization (hereinafter referred to as FIDA-PO).

FCS is an analytical method which analyzes fluctuations of fluorescence intensity for individual molecules of a fluorescent substance and is capable of analyzing relative sizes of individual molecules in the measured sample and proportions of molecules having various sizes (see, for example, Japanese Patent Publication No. 2001-272404). Since the unreacted primer has a smaller molecular size than that of a primer product, FCS allows one to measure with ease the ratio between the unreacted, fluorescently labeled primer and an amplified product in the reaction solution.

FIDA is an analytical method which is capable of determining fluorescence intensity for individual fluorescent molecules, and allows one to calculate quantities and proportions of molecules having different fluorescence intensities, in cases where two or more fluorescent molecules having different fluorescence intensities are present in the measured sample. Therefore, for example, when fluorescence intensity is different between the unreacted primer and a primer product, it is possible to observe fluorescence intensity for individual molecules, by FIDA and to measure with ease the ratio between the unreacted, fluorescently labeled primer and the amplified product in the reaction solution.

FIDA-PO is an analytical method in which FIDA and fluorescence polarization analysis are combined, and allows one to determine the degree of fluorescence polarization and the number of fluorescent molecules. FIDA-PO also allows one to calculate quantities and proportions of molecules having different degrees of fluorescence polarization, in cases where two or more fluorescent molecules having different degrees of fluorescence polarization are present in the measured sample. A primer product has a larger molecular size than that of the unreacted primer, resulting in a slower rotational movement, and thus has an increased degree of fluorescence polarization. Therefore, it is possible to observe the degree of fluorescence polarization for individual molecules by FIDA-PO and to measure with ease the ratio between the unreacted, fluorescently labeled primer and the amplified product in the reaction solution.

In the present invention, the PCR reaction of a target nucleic acid and the PCR reaction of a reference nucleic acid are independent to each other. Therefore, as described above, the detecting primer for target nucleic acid and the detecting primer for reference nucleic acid can be added to a single reaction solution to perform multiplex PCR, thereby to calculate the primer consumption rate of each primer, or alternatively a reaction solution containing a nucleic acid sample and a detecting primer for target nucleic acid, and a reaction solution containing the nucleic acid sample and a detecting primer for reference nucleic acid can be prepared separately to perform PCR with each of these reaction solutions under the identical reaction conditions, to thereby calculate the primer consumption rate of each primer.

Subsequently, in step (c), a first continuously differentiable function and a second continuously differentiable function are each calculated, wherein the first continuously differentiable function approximates the relationship between the mixing ratios of the standard nucleic acid samples used as a template and the amounts of amplified product derived from the target nucleic acid which are obtained in step (b), and wherein the second continuously differentiable function approximates the relationship between the mixing ratios and the amounts of amplified product derived from the reference nucleic acid which are obtained in step (b). Here, as the mixing ratio approaches one, the amount of amplified product derived from the target nucleic acid will become saturated, and on the contrary, as the mixing ratio approaches zero, the amount of an amplified product derived from the reference nucleic acid will become saturated. Therefore, if the measured values are plotted with mixing ratios as the abscissa and measured primer consumption rates as the ordinate, then a saturation curve will be obtained. The following describes its grounds.

With the assumption that the amplification efficiency of PCR reaction (that is, the efficiency of a primer consumption) is driven by the concentration of primer and when it is noted that the PCR reaction takes place by the extension reaction of an annealed pair of template and primer, the amount of primer decreased in each cycle can be expressed by the following equation (1) with the template concentration ([Product]), primer concentration ([Primer]), reaction efficiency (k), cycle number (c), wherein the template in the reaction solution includes amplified products obtained by the PCR reaction, in addition to the initial template which was added to the reaction solution:

[Equation 1]

$$\frac{d[\text{Primer}]}{dc} = -k[\text{Product}][\text{Primer}] \quad (1)$$

On the other hand, since the amount of template increased is equal to the amount of primer consumed, the equation (2) described below holds:

[Equation 2]

$$\frac{d[\text{Prduct}]}{dc} = -\frac{d[\text{Primer}]}{dc} \quad (2)$$

Figure 1:
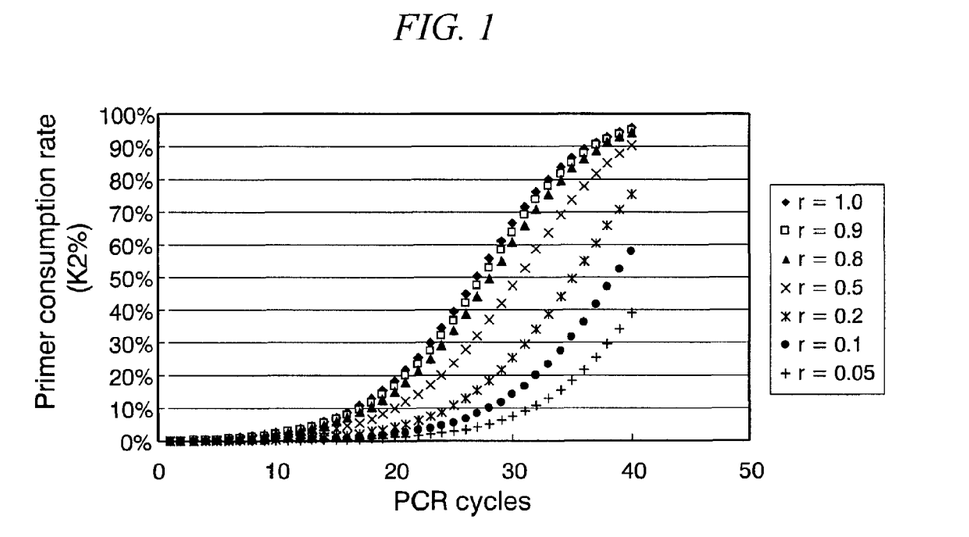
FIG. 1 represents a graph showing amplification curves of PCR reactions in the case where the assumption is made that the amplification efficiency of PCR is proportional to the concentrations of template and primer.

If these differential equations can approximate the efficiency of the subsequent reaction with the concentrations of template and primer in the previous cycle, then the following equations (3) and (4) will be given, respectively. By solving these differential equations analytically with Euler's procedure, an amplification curve of the PCR reaction will be determined depending on the initial template amount. Here, let the initial template amount be expressed as a mixing ratio (r), and an amplification curve of the PCR reaction of a target nucleic acid will be generated as shown in FIG. 1.

[Equation 3]

$$d[\text{Primer}] = -k[\text{Product}][\text{Primer}]dc \quad (3)$$

$$d[\text{Product}] = -d[\text{Primer}]dc \quad (4)$$

Figure 2:
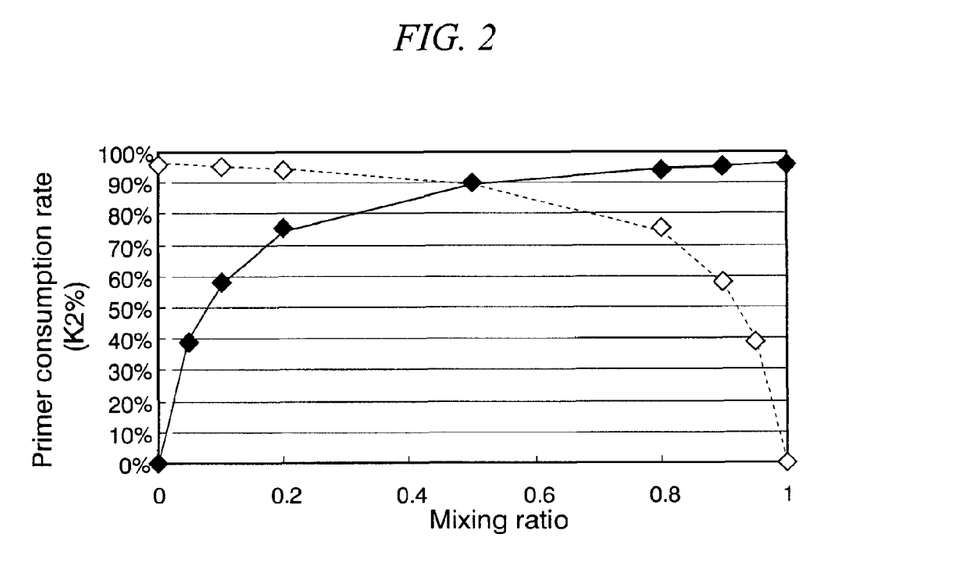
FIG. 2 represents a graph plotting primer consumption rates (K2%) at the 40th cycle of the amplification curve in FIG. 1 against mixing ratios (r). In the figure, "closed diamonds" and "open diamonds" denote primer consumption rates of the target nucleic acid and of the reference nucleic acid, respectively.

In general, the number of thermal cycles in the PCR reaction is 30 to 40 cycles. Thus, if the primer consumption rate (K2%) at the 40th cycle is plotted against the mixing ratio (r), then plotting will be done as shown by "closed diamonds" in FIG. 2, and it will be understood that in the PCR reaction of the target nucleic acid, the relationship between the mixing ratio (r) and the primer consumption rate (K2%) can be approximated to a saturation curve. In the PCR reaction of the reference nucleic acid, on the other hand, since the initial template amount of the reference nucleic acid is expressed as (1−r), as opposed to mixing ratio (r), plotting will be done as shown by "open diamonds" in FIG. 2, if the results from a similar analysis are plotted, and also in this case, the relationship between the mixing ratio (r) and the primer consumption rate (K2%) can be approximated to a saturation curve.

Therefore, the continuously differentiable functions obtained in step (c) are not limited specifically, if they are continuously differentiable functions which can approximate a saturation curve, and can be selected and employed as appropriate, from approximating equations employing generally in operational analysis. A first continuously differentiable function approximating the relationship between the mixing ratio (r) and the primer consumption rate of the detecting primer for target nucleic acid (K2%(T)), and a second continuously differentiable function approximating the relationship between mixing ratio (r) and the primer consumption rate of the detecting primer for reference nucleic acid (K2% (C)) can be, for example, continuously differentiable functions with the forms described below, where a, b, c, a', b', and c' are constants which are dependent upon reaction conditions:

A first continuously differentiable function: $K2\%(T) = ar/(b+r)+c$

A second continuously differentiable function: $K2\%(C) = a'(1-r)/\{b'+(1-r)\}+c'$ [Equation 4]

In addition, the following continuously differentiable functions of sixth degree polynomials may be used, where a, b, c, d, e, f, g, a', b', c', d', e', f', and g' are constants which are dependent upon reaction conditions:

A first continuously differentiable function: $K2\%(T) \leq ar^6+br^5+cr^4+dr^3+er^2+fr+g$ A second continuously differentiable function: $K2\%(C) = a'(1-r)^6+b'(1-r)^5+c'(1-r)^4+d'(1-r)^3+e'(1-r)^2+f'(1-r)+g'$ [Equation 5]

Also in step (d), the above-described steps (i) and (ii) are carried out on nucleic acid samples to be examined and the amount of amplified product derived from the target nucleic acid and the amount of amplified product derived from reference nucleic acid are measured. Specifically, these steps are carried out under conditions where the composition of reaction solutions and reaction conditions in the PCR reaction are the same as those in step (b) in all respects, except that a nucleic acid sample to be examined which is an objective to be analyzed is employed as a template, in place of the standard nucleic acid sample. Step (d) can be carried out independently of or simultaneously with step (b). In this case, because it is believed that most of the primer which has been consumed in the amplification reaction becomes an amplified product, the primer consumption rate would correspond with the amount of amplified product. As in step (b), therefore, it is possible to calculate the primer consumption rate of each of the detecting primer for target nucleic acid and the detecting primer for reference nucleic acid.

The nucleic acid samples to be examined which are employed in the present invention are not limited specifically, if they can be expected to contain a target nucleic acid and a reference nucleic acid. The nucleic acid samples to be examined may be living-body samples which are collected from animals and others, samples prepared form solutions of cultured cells and others, and solutions of genome extracted and/or purified from living-body samples and others. In particular, it is preferable that the nucleic acid samples to be examined are living-body samples derived from humans, which are employed for clinical examinations, and solutions of genome extracted and/or purified from living-body samples derived from humans. Living-body samples derived from humans include, for example, blood, bone marrow fluid, lymph, urine, sputum, ascitic fluid, exudate, amniotic fluid, intestinal lavage fluid, lung lavage fluid, bronchial lavage fluid, bladder lavage fluid, pancreatic juice, saliva, semen, bile, pleural fluid, nails, hairs, feces, and the like. The living-body samples may also be samples standing in the states when they were collected from living organisms, and prepared samples thereof. Methods for such preparation are not limited specifically, if they do not damage genome which is contained in living-body samples, and usually, preparation methods which are conducted on living-body samples can be carried out.

In the inventive methods for estimating the target nucleic acid ratio, it is preferable to employ nucleic acid samples to be examined which contain a target nucleic acid which is used as a template and a reference nucleic acid at sufficient amounts, in order to estimate the target nucleic acid ratio with higher accuracy. Therefore, it is preferable that, when living-body samples are employed as nucleic acid samples to be examined, a target nucleic acid and a reference nucleic acid are amplified in advance by PCR reaction or the like. For example, in cases where a nucleic acid derived from a gene to be examined which a mutated cell possesses is used as a target nucleic acid, a nucleic acid derived from a gene to be examined which a normal cell possesses is used as a reference nucleic acid, and a solution of genome extracted and/or purified from a living-body sample is used as a nucleic acid sample to be examined, it is preferable that nucleic acid of a partial region of the gene to be examined which contains a mutated site is amplified by PCR reaction and the resultant amplified product is used as the nucleic acid sample to be examined.

Figure 3:
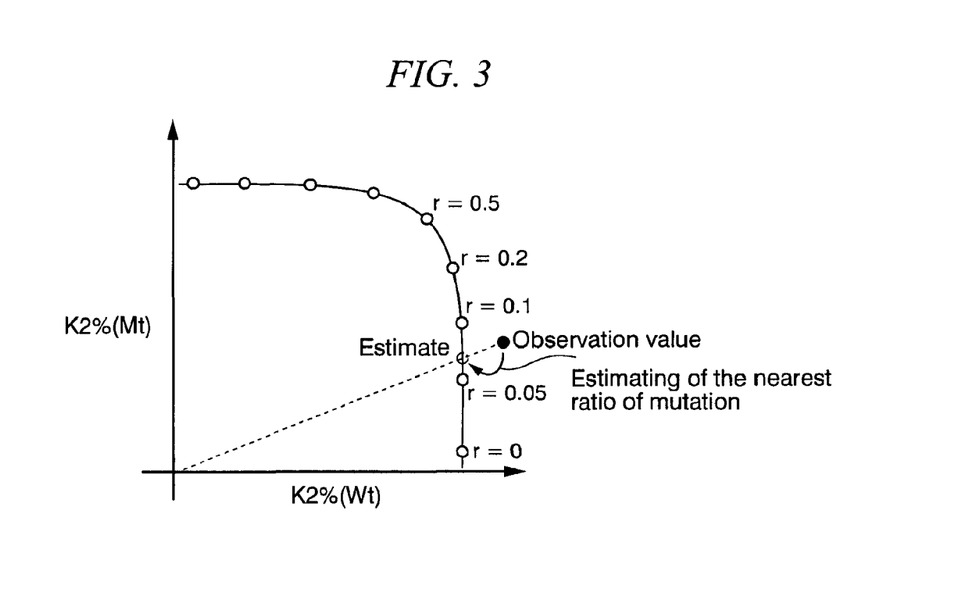
FIG. 3 represents a graph briefly showing the relationship between the mixing ratio, which is determined from the first continuously differentiable function and the second continuously differentiable function, the amount of reference nucleic acid, and the amount of target nucleic acid; and the method for estimating a target nucleic acid ratio in the examined sample.

Then, in step (e), the ratio of the target nucleic acid to the total amount of target nucleic acid and reference nucleic acid in the examined nucleic acid sample is estimated from the amount of amplified product derived from the target nucleic acid and the amount of amplified product derived from the reference nucleic acid which are obtained in step (d), and the first and second continuously differentiable functions which are obtained in the above-described step (c). For example, if plotting is done with mixing ratios (r) as a mediating parameter, using as the abscissa, primer consumption rates, K2% (T), of the detecting primer for target nucleic acid which are obtained from the first continuously differentiable function obtained in step (c) and as the ordinate, primer consumption rates, K2%(C), of the detecting primer for target nucleic acid which are obtained from the second continuously differentiable function, then a curve as shown in the solid line in FIG. 3 will be obtained. Thus, if from the first and second continuously differentiable functions, the relationship between the mixing ratio, and the amount of reference nucleic acid and the amount of target nucleic acid is represented by a curve which is shown in the solid line in FIG. 3, then it will be estimated that the mixing ratio (r) at a point on the curve which, using the distance from the origin as a variable, is nearest to the point at which the primer consumption rates of the detecting primer for target nucleic acid and the detecting primer for reference nucleic acid in the examined nucleic acid sample obtained in step (d) are plotted ("observation value" in FIG. 3), specifically, an point at which the line drawn at the point where the observation value is plotted and the origin intersects the curve ("estimate" in FIG. 3), is the target nucleic acid ratio in the examined nucleic acid sample.

As described above, in the inventive methods for estimating the target nucleic acid ratio, because the functions approximating the primer consumption rates of the detecting primer for target nucleic acid and of the detecting primer for reference nucleic acid are each separately and independently determined, it is possible to estimate from both functions the relationship between the mixing ratio, and the amount of reference nucleic acid and the amount of target nucleic acid, even in cases where the amplification efficiency of a target nucleic acid (primer consumption rate) and the amplification efficiency of a reference nucleic acid are significantly different.

EXAMPLES

The present invention is further described in detail with reference to examples and is not intended to be limited to the following examples.

Example 1

Figure 4:
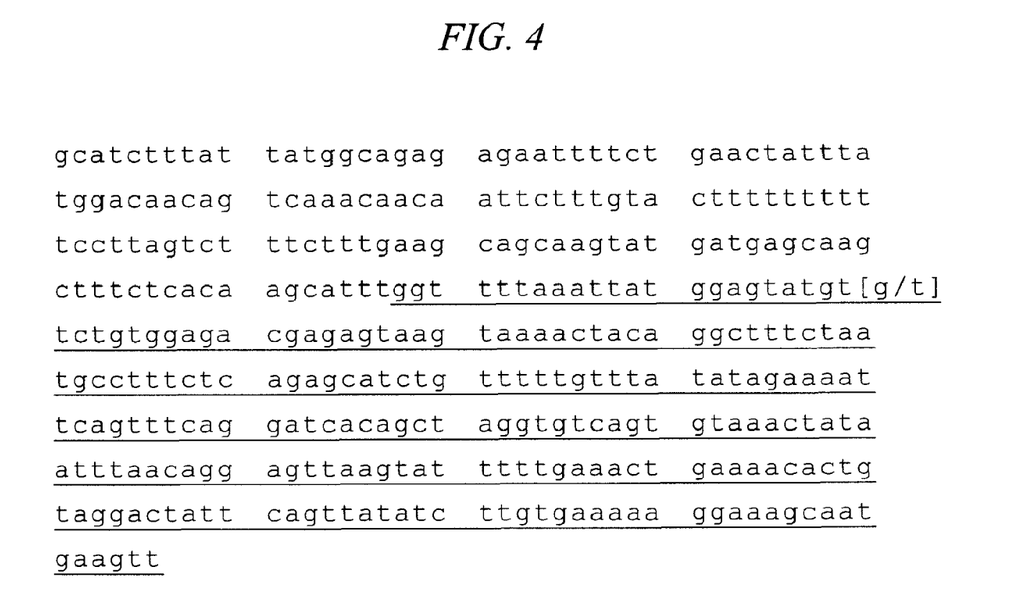
FIG. 4 represents a nucleotide sequence around V617F of the JAK2 gene (SEQ. ID NO: 5).

The mutation ratio of the mutation V617F of the JAK2 gene which is detected at high frequencies in tumor cells was estimated employing the inventive method for estimating a target nucleic acid ratio. This somatic mutation is a mutation in which the third base G of the codon GTG coding for valine, the 617th residue of the JAK2 gene, is mutated to T, resulting in phenylalanine. FIG. 4 shows the nucleotide sequence around the V617F in the JAK2 gene. In the nucleotide sequence, the underlined site was used as a target nucleotide sequence or as a reference nucleotide sequence in this example. In the figure, [G/T] is the mutated site, the nucleotide sequence in which the mutated site was G was used as a reference nucleic acid and the nucleotide sequence in which the mutated site was T was used as a target nucleic acid.

(Standard Nucleic Acid Sample Series)

Nucleic acids having the target nucleotide sequence and the reference nucleotide sequence shown in FIG. 4 were mixed to prepare a standard nucleic acid sample series consisting of nine standard nucleic acid samples, so that the respective mixing ratios (ratios of the amount of target nucleic acid to the total amount of target nucleic acid and reference nucleic acid) were 0, 0.05, 0.1, 0.2, 0.5, 0.8, 0.9, 0.95, and 1.0. The target nucleic acid and reference nucleic acid employed for preparing the standard nucleic acid samples used nucleic acids obtained by PCR amplifying a nucleic acid having the nucleotide sequence shown in FIG. 4 with a forward primer (1st-Fw-Primer) and a reverse primer (1st-Rv-Primer) shown in Table 1, confirming the nucleotide sequence of the resultant amplified products, and then inserting it into a plasmid.

TABLE 1

| Primer | Seq |
|---|---|
| Fw-Primer (SEQ ID NO:1) | CATCTTTATTATGGCAG |
| Rv-Primer (SEQ ID NO:2) | AACTTCATTGCTTTCC |

In addition, in order to increase the amount of template to sufficient amounts, PCR was performed using each of the standard nucleic acid samples as the template with 1st-Fw-Primer and 1st-Rv-Primer to amplify the target nucleic acid and the reference nucleic acid. This amplification treatment has no effect on mixing ratios, because the same primers were employed.

Specifically, to 10 μL of 2× AmpliTaq Gold Master Mix (ABI) was added each of the standard nucleic acid samples, so that the total amount of target nucleic acid and reference nucleic acid was 4,000 copies (an amount corresponding to about 20 ng of genome DNA), and each of 1st-Fw-Primer and 1st-Rv-Primer was further added, so that the final concentration was 0.5 μM, and the final volume was adjusted to 20 μL with milliQ water to prepare reaction solutions. PCR reactions were performed under reaction conditions which consisted of the steps of treating the reaction solutions at 95° C. for 10 minutes, followed by subjecting the reaction solutions to 40 cycles of 95° C. for 30 seconds, 54° C. for 30 seconds, and 72° C. for 30 seconds, and further treating the reaction solutions at 72° C. for 10 minutes. The PCR reactions were performed employing a Thermal Cycler PTC-200 (MJ). The reaction solutions after the PCR reactions were used as post-amplification standard nucleic acid samples.

(First and Second Continuously Differentiable Functions)

Reaction solutions were prepared which used the post-amplification standard nucleic acid samples as the template and contained a detecting primer for target nucleic acid which was labeled with TAMR at the 5' end (T-Fw-Primer) and a detecting primer for reference nucleic acid which was labeled with ATTO 647N at the 5' end (G-Fw-Primer), and PCR was performed to measure the primer consumption rates of each of the primers to determine first and second continuously differentiable functions. The nucleotide sequences of the detecting primers are shown in Table 2. As the reverse primer, an Rv-Primer was continuously employed which was carried over into the reaction solutions from the post-amplification standard nucleic acid samples.

TABLE 2

| Primer | Seq |
|---|---|
| T-Fw-Primer (SEQ ID NO:3) | TTTTAAATTATGGAGTATGTT |
| G-FW-Primer (SEQ ID NO:4) | GGTTTTAAATTATGGAGTATGTG |

Specifically, to 2 μL of 10× Stoffel Fragment Buffer (ABI) were added 1 μL of post-amplification standard nucleic acid sample, magnesium sulfate (a final concentration of 2.5 mM), each dNTP (a final concentration of 0.2 mM), T-Fw-Primer (a final concentration of 0.5 μM), G-Fw-Primer (a final concentration of 0.5 μM), and 0.1 U of Stoffel Fragment (ABI), and the final volume was adjust to 20 μL with milliQ water to prepare reaction solutions. As negative control, a reaction solution was also prepared which had the same volume of MilliQ water added thereto, instead of the standard nucleic acid sample. PCR reactions were performed under reaction conditions which consisted of the steps of treating the reaction solutions at 95° C. for 10 minutes, followed by subjecting the reaction solutions to 40 cycles of 95° C. for 30 seconds, 52° C. for 60 seconds, and 72° C. for 30 seconds, and further treating the reaction solutions at 72° C. for 10 minutes. The PCR reactions were performed employing a Thermal Cycler PTC-200 (MJ).

The reaction solutions after the PCR reactions were diluted 100 times with 10 mM Tris buffer, and FCS measurement was carried out employing a fluorescence correlation spectroscopy apparatus MF-20 (Olympus Corporation). Measuring was done for 15 seconds three times on each of the samples and their average value was expressed as the measured result. Components having short diffusion times obtained as the results of measuring were considered to represent the unreacted primer and components having long diffusion times were considered to represent amplified products, and the ratio between both components was determined and then used to calculate the primer consumption rate (K2%).

Figure 5:
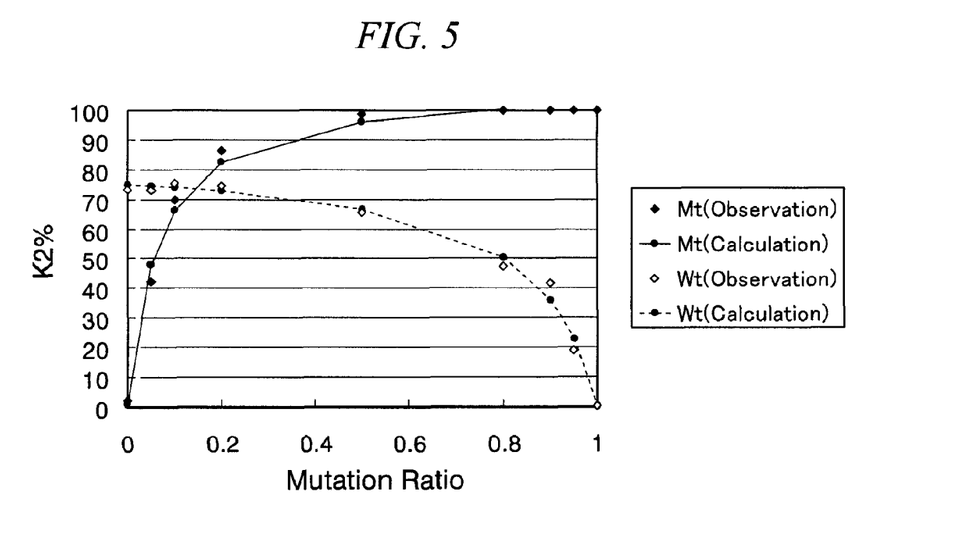
FIG. 5 represents a graph plotting primer consumption rates (K2%) of the respective primers measured in Example 1 against mixing ratios (r). In the figure, "closed diamonds" and "open diamonds" denote primer consumption rates of the target nucleic acid and of the reference nucleic acid, respectively.

FIG. 5 is a plot of calculated primer consumption rates (K2%) of the respective primers against mixing ratios (r). In the figure, the "closed diamonds" and "open diamonds" indicate primer consumption rates of target nucleic acid and of reference nucleic acid, respectively. These measured results was subjected to fitting with the equations described below to determine the continuously differentiable function of primer consumption rate K2%(T) of the detecting primer for target nucleic acid, K2%(T)=$F_1(r)$, and the continuously differentiable function of primer consumption rate K2%(G) of the detecting primer for target nucleic acid, K2%(G)=$F_1'(1-r)$. In FIG. 5, the solid line represents K2%(T) $F_1(r)$ and the dotted line represents K2%(G)=$F_1'(1-r)$.

There is a high correlation between the measured values and the following functions and the results of fitting are as shown in Table 3. The diagrammatic meanings of a (a'), b (b'), and c (c') are a: a value at which K2% reaches the saturation, b:a mutation ratio at which K2% reaches half the saturation, and c:a signal at a mutation ratio of 0%, respectively.

$$K2\%(T)=ar/(b+r)+c$$

$$K2\%(G)=a'(1-r)/\{b'+(1-r)\}+c' \qquad [\text{Equation 6}]$$

TABLE 3

| Parameter | K2% (T) | K2% (G) |
|---|---|---|
| a or a' | 107.23 | 84.94 |
| b or b' | 0.06 | 0.14 |
| c or c' | 1.07 | 0.39 |
| Corr | 1.00 | 0.99 |

Figure 6:
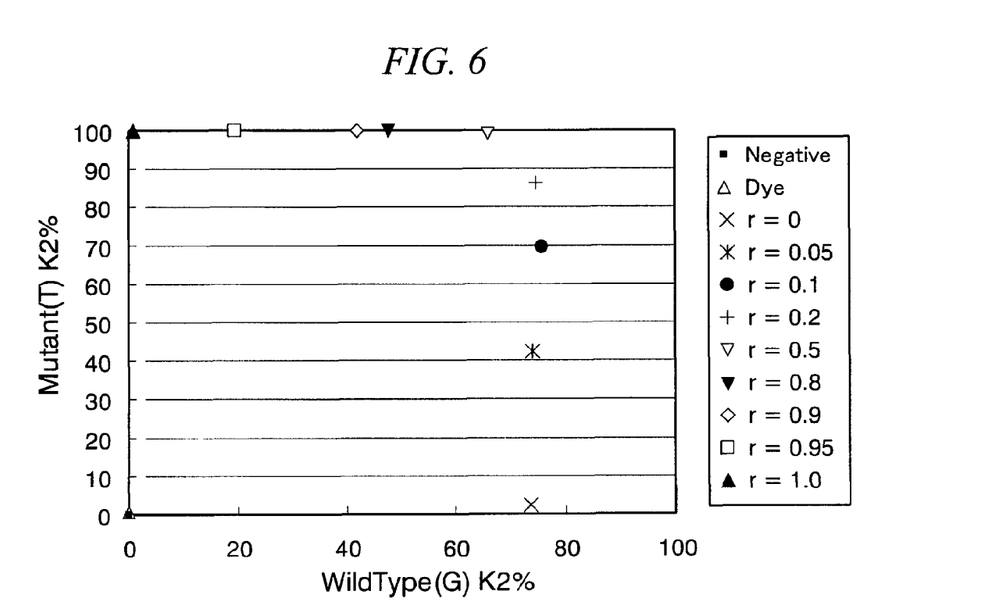
FIG. 6 represents a graph showing the relationship between the mixing ratio, which is determined from the first continuously differentiable function and the second continuously differentiable function obtained in Example 1, the amount of reference nucleic acid, and the amount of target nucleic acid.

The curve shown in the solid line in FIG. 6 indicates the relationship between the mixing ratio, and the amount of reference nucleic acid and the amount of target nucleic acid, which was determined from the resultant first and second continuously differentiable functions. The abscissa (Mutant (T) K2%) represents the primer consumption rate of the detecting primer for target nucleic acid and the ordinate (WildType(G) K2%) represents the primer consumption rate of the detecting primer for reference nucleic acid. In the figure, "Negative" and "Dye" show the results of the negative control (a reaction solution having no addition of standard nucleic acid sample) and of the dye for adjusting the apparatus in FCS measurements, respectively.

(Estimation of the Target Nucleic Acid Ratio Employing Measurement Samples with Known Ratios of Target Nucleic Acid)

In order to confirm that target nucleic acid ratios in samples can be estimated by employing the relationship between the mixing ratio, and the amount of reference nucleic acid and the amount of target nucleic acid, which is shown in the curve obtained in the above-described section, estimating target nucleic acid ratios was carried out from the resultant curve, employing measurement samples with known ratios of target nucleic acid.

The measurement samples with known ratios of target nucleic acid employed solutions prepared by mixing a target nucleic acid solution which was ascertained by sequencing to contain only the target nucleic acid, and a reference nucleic acid solution which was also ascertained by sequencing to contain only the reference nucleic acid, so that the respective mixing ratios were 0, 0.05, 0.1, 0.2, 0.5, 0.8, 0.9, 0.95, and 1.0. The copy number in each of the measurement samples was determined from UV absorption of its concentrated stock solution.

Figure 7:
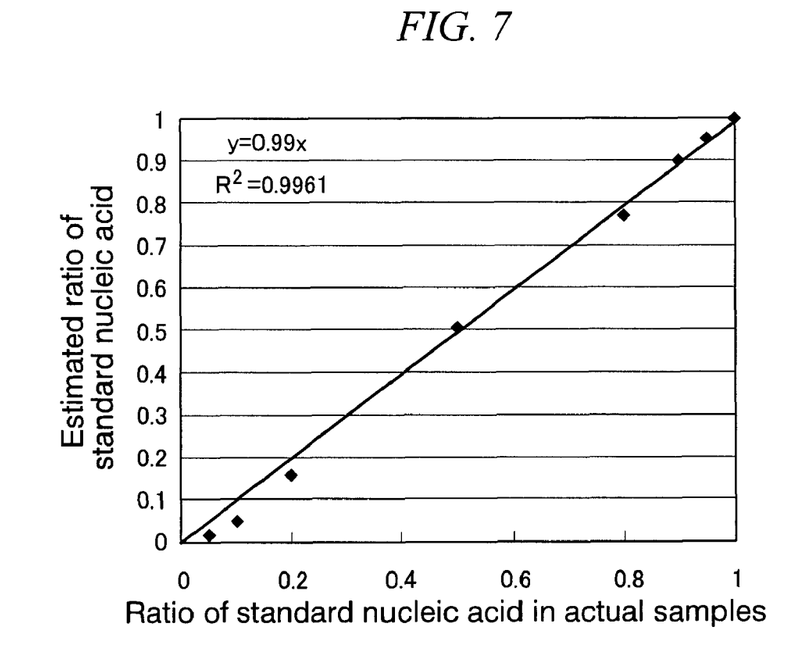
FIG. 7 represents a graph showing the relationship between the actual ratios and the ratios obtained as the results of measuring of the target nucleic acid in Example 1.

On the six measurement samples prepared, PCR reactions were performed as described above in the section "First and Second Continuously Differentiable Functions," to determine the primer consumption rate of each primer. The target nucleic acid ratio was estimated in a way described for FIG. 3 from the measured observation values and the curve shown in FIG. 6. Measuring was done 18 times on each of the measurement samples. The estimated target nucleic acid ratios and the actual target nucleic acid ratios were correlated, and had a slope of 0.982 (SD, 0.025) and a correlation coefficient of 0.988 (SD, 0.012), indicating that there was a high correlation. FIG. 7 shows the relationship between the actual target nucleic acid ratios and the target nucleic acid ratios obtained as the results of measuring. Therefore, it is apparent from these results that the inventive method for estimating a target nucleic acid ratio can be used to estimate simply and with high accuracy the target nucleic acid ratio in the examined nucleic acid samples.

Example 2

It was demonstrated that the inventive method for estimating a target nucleic acid ratio enables one to estimate the target nucleic acid ratio, even when the relationship between the primer consumption rate (K2%) and the mixing ratio (r) was approximated to different continuously differentiable functions from those in Example 1.

Specifically, primer consumption rates (K2%) of each primer obtained in the section "First And Second Continuously Differentiable Functions" in Example 1 were plotted against mixing ratios (r) as in FIG. 5, followed by carrying out fitting with the equations described below, to determine a continuously differentiable function of primer consumption rate K2%(T) of the detecting primer for target nucleic acid, K2%(T)=$F_2(r)$, and a continuously differentiable function of primer consumption rate K2%(G) of the detecting primer for target nucleic acid, K2%(G)=$F_2'(1-r)$. There is a high correlation between the measurements and the functions described below and the results of the fitting are as shown in Table 4. A curve showing the relationship between the mixing ratio, and the amount of reference nucleic acid and the amount of target nucleic acid was obtained as in FIG. 3, employing the resultant functions, K2%(T)=$F_2(r)$ and K2%(G)=$F_2'(1-r)$.

$$K2\%(T)=ar^6+br^5+cr^4+dr^3+er^2+fr+g$$

$$K2\%(G)=a'(1-r)^6+b'(1-r)^5+c'(1-r)^4+d'(1-r)^3+e'(1-r)^2+f'(1-r)+g' \quad \text{[Equation 7]}$$

TABLE 4

| Parameter | K2% (T) | K2% (G) |
|---|---|---|
| a or a' | −36.4207 | −337.145 |
| b or b' | −264.107 | 139.722 |
| c or c' | 224.9926 | 446.6424 |
| d or d' | 829.5614 | 266.5907 |
| e or e' | −1215.58 | −967.415 |
| f or f' | 536.0907 | 500.6358 |
| g or g' | 8.576492 | 5.069187 |
| Corr | 0.987766 | 0.995755 |

Figure 8:
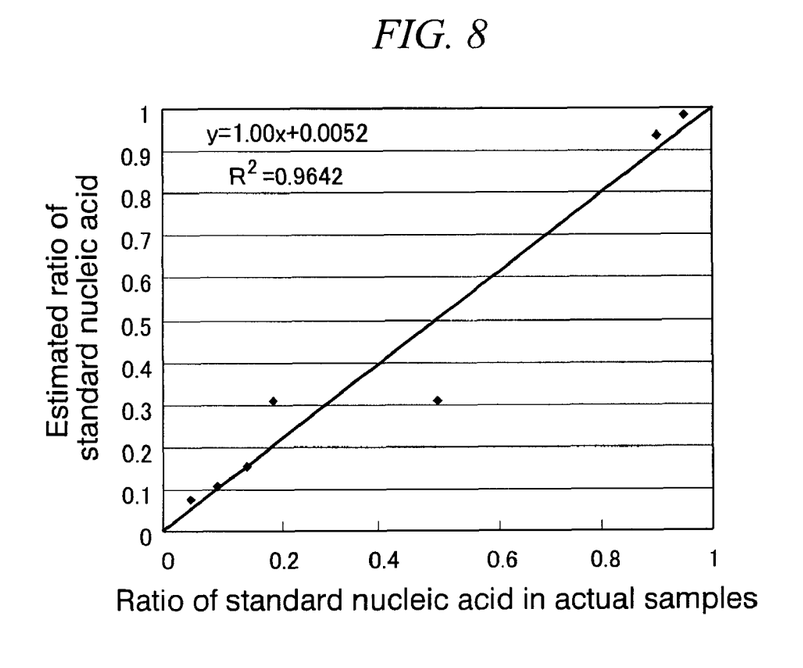
FIG. 8 represents a graph showing the relationship between the actual ratios and the ratios obtained as the results of measuring of the target nucleic acid in Example 2.

On six measurement samples having known ratios of target nucleic acid which were prepared in Example 1, PCR reactions were performed in a similar way, to determine the primer consumption rate of each primer. The target nucleic acid ratio was estimated in a way described for FIG. 3 from the measured observation values and the curve obtained in the above-described section. Measuring was done 18 times on each of the measurement samples. The estimated target nucleic acid ratios and the actual target nucleic acid ratios were correlated, and had a correlation coefficient of 0.96, indicating that there was a high correlation. FIG. 8 shows the relationship between the actual target nucleic acid ratios and the target nucleic acid ratios obtained as the results of measuring. Therefore, it is apparent from these results that in step (c) of the inventive method for estimating a target nucleic acid ratio, the continuously differentiable functions approximating the relationship between the primer consumption rate and the mixing ratio are any function which could generally approximate a saturation curve, and the target nucleic acid ratio in the examined nucleic acid samples can be estimated simply and with high accuracy, even if any function is employed for approximation.

The inventive method for estimating a target nucleic acid ratio is particularly useful in the field of clinical examinations, such as analysis of somatic mutations associated with tumors that estimates the ratio of a mutated cell in samples, because the present method can be employed to determine the ratio between the amount of target nucleic and the amount of reference nucleic acid simply and with high accuracy also at the endpoint of PCR.

What is claimed is:

1. A method for estimating a molar ratio of a target nucleic acid to a total amount of the target nucleic acid and a reference nucleic acid in a test sample, the method comprising:

(a) preparing a plurality of standard nucleic acid samples, each having a different predetermined molar ratio of the target nucleic acid to the total amount of the target nucleic acid and the reference nucleic acid;

(b) performing a Polymerase Chain Reaction (PCR) reaction on each of said plurality of standard nucleic acid samples using (1) one of said plurality of standard nucleic acid samples, (2) a primer pair including a detecting primer for the target nucleic acid, and (3) a primer pair including a detecting primer for the reference nucleic acid;

(c) measuring an amount of amplified target nucleic acid product and an amount of amplified reference nucleic acid product in each of said plurality of standard nucleic acid samples;

(d) calculating a first continuously differentiable function which approximates the relationship between the predetermined molar ratios and a consumption rate of the detecting primer for the target nucleic acid, in each of said plurality of standard nucleic acid samples after step (b);

(e) calculating a second continuously differentiable function which approximates the relationship between the predetermined molar ratios and a consumption rate of the detecting primer for the reference nucleic acid in each of said plurality of standard nucleic acid samples after step (b);

(f) performing a Polymerase Chain Reaction (PCR) reaction on a test sample in using (1) the test sample, (2) the primer pair including the detecting primer for the target nucleic acid, and (3) the primer pair including the detecting primer for the reference nucleic acid;

(g) measuring an amount of amplified target nucleic acid product and an amount of amplified reference nucleic acid product in the test sample;

(h) estimating the molar ratio of the target nucleic acid to the total amount of the target nucleic acid and the reference nucleic acid in the test sample based on (1) the first continuously differentiable function, (2) the second continuously differentiable function, (3) the primer consumption rate of the detecting primer for the target nucleic acid in the test sample, and (4) the primer consumption rate of the detecting primer for the reference nucleic acid product in the test sample.

2. The method for estimating a target nucleic acid ratio according to claim 1,
wherein step (b) includes the steps of
(b1) performing a PCR reaction in a reaction solution containing (1) one of said plurality of standard nucleic acid samples and (2) the primer pair including the detecting primer for the target nucleic acid, and
(b2) performing a PCR reaction in a reaction solution containing (1) one of said plurality of standard nucleic acid samples and (2) the primer pair including the detecting primer for the reference nucleic acid,
wherein steps (b1) and (b2) are performed separately, and
wherein the step (f) includes the steps of
(f1) performing a PCR reaction in a reaction solution containing (1) the test sample and (2) the primer pair including the detecting primer for the target nucleic acid, and
(f2) performing a PCR reaction separately in a reaction solution containing (1) the test sample and (2) the primer pair including the detecting primer for the reference nucleic acid,
wherein steps (f1) and (f2) are performed separately.

3. The method for estimating a target nucleic acid ratio according to claim 1, wherein the detecting primer for the target nucleic acid and the detecting primer for the reference nucleic acid are primers labeled with fluorescent substances.

4. The method for estimating a target nucleic acid ratio according to claim 3, wherein steps (c) and (g) are carried out by employing one or more analyses selected from the group consisting of fluorescence correlation spectroscopy, fluorescence intensity distribution analysis, and fluorescence intensity distribution analysis-polarization.

5. The method for estimating a target nucleic acid ratio according to claim 1, wherein steps (c) and (g) are carried out by employing a DNA binding dye.

6. The method for estimating a target nucleic acid ratio according to claim 1, wherein steps (c) and (g) are carried out by employing a hybridization probe labeled with a fluorescent substance.

7. The method for estimating a target nucleic acid ratio according to claim 1, wherein steps (c) and (g) are carried out by employing a FRET hybridization probe, a molecular beacon, or a TaqMan probe.

8. The method for estimating a target nucleic acid ratio according to claim 1, wherein the target nucleic acid is a nucleic acid derived from a mutated cell and the reference nucleic acid is a nucleic acid derived from a normal cell.

9. The method for estimating a target nucleic acid ratio according to claim 1,
wherein the target nucleic acid is a nucleic acid derived from a mutated gene, and
wherein the reference nucleic acid is a nucleic acid derived from a normal counterpart of the mutated gene.

10. The method for estimating a target nucleic acid ratio according to claim 9, wherein the gene to be examined is a gene selected from the group consisting of the Epidermal Growth Factor Receptor (EGFR) gene, the JAK2 gene, and the Bcr-Ab1 gene.

11. The method for estimating a target nucleic acid ratio according to claim 1,
wherein the target nucleic acid is a nucleic acid having a sequence comprising a first polymorphism at a polymorphic site, and
wherein the reference nucleic acid is a nucleic acid having a sequence comprising a second polymorphism at the polymorphic site.

12. The method for estimating a target nucleic acid ratio according to claim 11, wherein the genetic polymorphisms are single nucleotide polymorphisms.

13. The method for estimating a target nucleic acid ratio according to claim 11, wherein the gene polymorphisms are mitochondrial DNA polymorphisms.

14. The method for estimating a target nucleic acid ratio according to claim 1, wherein the target nucleic acid is a nucleic acid derived from a parasitic organism and the reference nucleic acid is a nucleic acid derived from a host organism.

15. The method for estimating a target nucleic acid ratio according to claim 14, wherein the parasitic organism is a bacterium or a virus.

16. The method for estimating a target nucleic acid ratio according to claim 1, wherein the target nucleic acid is a nucleic acid derived from a genetically modified plant and the reference nucleic acid is a nucleic acid derived from a genetically non-modified plant.

17. The method of claim 1, wherein step (h) includes
(h1) plotting a graph having the primer consumption rate of said detecting primer for the target nucleic acid and the primer consumption rate of said detecting primer for the reference nucleic acid as axes and including a curve obtained from said first continuously differentiable function and said second continuously differentiable function with said predetermined mixing ratios as a mediating parameter; and
(h2) estimating the molar ratio of the target nucleic acid to the total amount of the target nucleic acid and the reference nucleic acid in the test sample by plotting a data point corresponding to said primer consumption rate of the detecting primer for the target nucleic acid and said primer consumption rate of the detecting primer for the reference nucleic acid, and estimating the molar ratio of the target nucleic acid to the total amount of the target nucleic acid and the reference nucleic acid in the test sample as the molar ratio on said curve which is either (i) nearest to said data point or (ii) an intersection point between said curve and a straight line drawn between the origin of the graph and said data point.

18. The method of claim 2, wherein step (h) includes (h1) plotting a graph having the primer consumption rate of said detecting primer for the target nucleic acid and the primer consumption rate of said detecting primer for the reference nucleic acid as axes and including a curve obtained from said first continuously differentiable function and said second continuously differentiable function with said predetermined mixing ratios as a mediating parameter; and (h2) estimating the molar ratio of the target nucleic acid to the total amount of the target nucleic acid and the reference nucleic acid in the test sample by plotting a data point corresponding to said primer consumption rate of the detecting primer for the target nucleic acid and said primer consumption rate of the detecting primer for the reference nucleic acid, and estimating the molar ratio of the target nucleic acid to the total amount of the target nucleic acid and the reference nucleic acid in the test sample as the molar ratio on said curve which is either (i) nearest to said data point or (ii) an intersection point between said curve and a straight line drawn between the origin of the graph and said data point.

* * * * *

SEQUENCE LISTING

<160> NUMBER OF SEQ ID NOS: 5

<210> SEQ ID NO 1
<211> LENGTH: 17
<212> TYPE: DNA
<213> ORGANISM: Artificial Sequence

```
-continued

<220> FEATURE:
<223> OTHER INFORMATION: Description of Artificial Sequence: Fw-Primer.

<400> SEQUENCE: 1
catctttatt atggcag                                                17

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Rv-Primer.

<400> SEQUENCE: 2
aacttcattg ctttcc                                                 16

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      T-Fw-Primer.

<400> SEQUENCE: 3
ttttaaatta tggagtatgt t                                           21

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:
      G-Fw-Primer.

<400> SEQUENCE: 4
ggttttaaat tatggagtat gtg                                         23

<210> SEQ ID NO 5
<211> LENGTH: 366
<212> TYPE: DNA
<213> ORGANISM: human
<220> FEATURE:
<223> OTHER INFORMATION: nucleotide sequence around V617F of the JAK2
      gene.

<400> SEQUENCE: 5
gcatctttat tatggcagag agaattttct gaactattta tggacaacag tcaaacaaca    60
attctttgta cttttttttt tccttagtct ttctttgaag cagcaagtat gatgagcaag   120
ctttctcaca agcatttggt tttaaattat ggagtatgtk tctgtggaga cgagagtaag   180
taaaactaca ggctttctaa tgcctttctc agagcatctg tttttgttta tatagaaaat   240
tcagtttcag gatcacagct aggtgtcagt gtaaactata atttaacagg agttaagtat   300
ttttgaaact gaaaacactg taggactatt cagttatatc ttgtgaaaaa ggaaagcaat   360
gaagtt                                                             366
```